US006890311B2

(12) United States Patent
Love et al.

(10) Patent No.: US 6,890,311 B2
(45) Date of Patent: *May 10, 2005

(54) METHODS FOR PERFORMING MEDICAL PROCEDURES WITHIN A BREAST DUCT

(75) Inventors: Susan M. Love, Pacific Palisades, CA (US); Sanford H. Barsky, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 10/099,439

(22) Filed: Mar. 15, 2002

(65) Prior Publication Data

US 2002/0160431 A1 Oct. 31, 2002

Related U.S. Application Data

(63) Continuation-in-part of application No. 09/153,564, filed on Sep. 15, 1998, now Pat. No. 6,455,027, which is a continuation-in-part of application No. 08/931,786, filed on Sep. 16, 1997, now Pat. No. 6,168,779, and a continuation-in-part of application No. 09/740,561, filed on Dec. 19, 2000, now abandoned, which is a continuation of application No. 09/067,661, filed on Apr. 28, 1998, now Pat. No. 6,221,622.

(51) Int. Cl.[7] .............................................. A61B 5/00
(52) U.S. Cl. ....................................... 600/576; 600/581
(58) Field of Search ............................. 600/585, 581, 600/576, 573, 104; 128/897, 898

(56) References Cited

U.S. PATENT DOCUMENTS

| | | |
|---|---|---|
| 2,771,072 A | 11/1956 | Montaugé |
| 3,608,540 A | 9/1971 | Sartorius |
| 3,786,801 A | 1/1974 | Sartorius |
| 4,775,620 A | 10/1988 | Cardiff et al. |
| 5,413,558 A | 5/1995 | Paradis |
| 5,650,317 A | 7/1997 | Chang et al. |
| 5,728,537 A | 3/1998 | Silen et al. |
| 5,763,415 A | 6/1998 | Sukumar |
| 5,851,830 A | 12/1998 | Imam et al. |
| 6,168,779 B1 | 1/2001 | Barsky et al. |
| 6,221,622 B1 * | 4/2001 | Love |
| 6,328,709 B1 | 12/2001 | Hung et al. |
| 6,413,228 B1 | 7/2002 | Hung et al. |
| 6,500,114 B1 | 12/2002 | Petitto et al. |

FOREIGN PATENT DOCUMENTS

| | | |
|---|---|---|
| EP | 0 502 485 B | * 10/1996 |
| WO | WO 97/05898 | 2/1997 |
| WO | WO 99/13917 | 3/1999 |

OTHER PUBLICATIONS

Leborgne, Intraductal Biopsy of Certain Pathologic Processes of the Breast, Surgery 19:47–54 (1946).
Papanicolaou et al., Exfoliative Cytology of the Human Mammary Gland and Its Value in the Diagnosis of Cancer and Other Diseases of the Breast, Cancer 11:377–409 (1958).
Buehring, Screening for Breast Atypias Using Exfoliative Cytology, Cancer 43(5):1788–1799 (1979).
Jin et al., Study of Tumor Markers in Mammary Ductal Lavage for Early Detection of Breast Carcinoma, Zhongguo Zhong Liu Lin Chuang 23(6):381–385 (1996), with English translation.

(Continued)

Primary Examiner—Mary Beth Jones
Assistant Examiner—David J. McCrosky
(74) Attorney, Agent, or Firm—Gates & Cooper LLP

(57) ABSTRACT

Methods for performing medical procedures within the duct of a breast are described. An exemplary embodiment of the invention includes the steps of introducing a guiding member into a breast duct; introducing and positioning a member having an internal lumen in the breast duct; introducing a wash fluid into the breast duct through the internal lumen; removing washings from the breast duct through the internal lumen; and collecting the washings for cytological analysis.

19 Claims, 4 Drawing Sheets

OTHER PUBLICATIONS

Sauter et al., Nipple Aspirate Fluid: A Promising Non–Invasive Method to Identify Cellular Markers of Breast Cancer Risk, British J. Cancer 76(4):494–501 (1997).

M. Cukierfain et al., "Intragalactophoric Aspiration: Description of a Cytologic Examination Complementary to Galactography and First Results Obtained," J. belge Radiol.—Belgisch Tijdschr. Radiol., 1983, 66: 101–106.

Allen et al., PNAS, 1984, 81: 1203–1207, abstract.

S.H. Barsky et al., "Pathologic Analysis of Breast Duct Endoscoped Mastectomies," Laboratory Investigation, Modern Pathology, Annual Meeting Abstracts, 1996, Abstract 1090 67: pp. 15A.*

Bjorn–Hansen, R. Br. J. Radiol., 1965, 38: 947–951.*

Cardenosa et al., AJR Am. J. Roentgenol, 1994, 162: 1081–1087, abstract.*

Choudhury et al., Arch. Surg., 1989, 124: 874–875, abstract.*

Dairkee et al., J. Natl. Cancer Inst., 1988, 80: 691–695, abstract.*

C. Fabian et al., "Prevalence of Abnormal Biomarkers in Fine Needle Breast Aspirates in a High Risk Population: Potential for Use in Risk Prediction," Proc. Ann. Meet. Am. Assoc. Cancer Res., 1993, 34: A1556.*

C. Fabian et al., "Biomarker and Cytologic Abnormalities in Women at High and Low Risk for Breast Cancer," Jnl. of Cell. Biochem., 1993, 17G: 153–160.*

M. Falardeau et al., "Selective Galactophorectomy for Mono–Orificial Nipple Discharge Without Associated Mass: Technique and Results. Apropos of Seventy–Three Cases," Annales de Chirurgie, 1991, 45(9): 796–801.*

C. Feige, "Dynamic Morpho–Cyto–Echography and the Ecographic Galactoscopy Endoductal Sample. Intrinsic and Extrinsic Markers in the Detection of Breast Cancers," Ultrasound Med. Biol., 1982, vol. 14 Supp. 1: 97–108.*

J. A. Fisher, "Our Medical Future: Breakthroughs in Health and Longevity by the Year 2000 and Beyond," 1992, Pocket Books, New York, NY, pp. 136–141.*

Grillo et al., Ann. Chir. Cynaecol., 1990, 79(1): 6–9.*

Guelstein et al., Int. J. Cancer, 1988, 42: 147–153, abstract.*

Heatley et al., J. Clin. Pathol., 1995, 48: 26–32, abstract.*

M.F. Hou et al., "A Simple Method of Duct Cannulation and Localization for Galactography Before Excision in Patients with Nipple Discharge," Radiology, 1995, 195(2): 568–569.*

S. Imayama et al., "Presence of Elevated Carcinoembryonic Antigen on Absorbent Disks Applied to Nipple Area of Breast Carcinoma Patients," Cancer, 1996, 78(6): 1229–1234.*

Jarasch et al., Human Pathol., 1988, 19: 276–289, abstract.*

Karesen et al., Tidsskr. Nor Laegeforen, 1993, 113: 1233–1235, Abstract.*

T. Katamine et al., "Determination of Cancer–Associated Antigens in Body Fluid Secreted from Nipple," Chemical Abstracts, 1991, 114(9): 2pp.*

R.A. Leborgne, "The Breast in Roentgen Diagnosis," Impressora Uruguaya S.A.—Juncal [51], Montevideo, Uruguay, 1953.*

R. Lewis, "Technique Probes Breast Ducts for Cancer Cells," Biophotonics International, 1997, pp. 27–28.*

S. Love, "Breast Duct Endoscopy: A Pilot Study of a Potential Technique for Evaluating Intraductal Disease," 15th Ann. San Antonio Breast Cancer Symp., San Antonio, TX, 1996, Abstract #197, p. 180.*

S. Love et al., "Breast–Duct Endoscopy to Study Stages of Cancerous Breast Disease," The Lancet, 1996, 348: 997–999.*

M. Makita et al, "Duct Endoscopy and Endoscopic Biopsy in the Evaluation of Nipple Discharge," Breast Cancer Research and Treatment, 1991, 18: 179–187.*

Nagle et al., Histochem. Cytochem., 1986, 34: 869–881, abstract.*

S. Naran et al., "Cytologic Diagnosis of Papillary Carcinoma of the Breast in Needle Aspirates," Diagnostic Cytopathology, 1988, 4(1): 33–37.*

A. Okazaki, "Diagnosis of Nonpalpable Breast Cancer by Ductoscopy: Comparison of Imaging and Histological Findings," Nyugan no Rinsho (Clinical Breast Cancer), 1989, 4(4): 587–594.*

A. Okazaki et al., "Fiberoptic Ductoscopy of the Breast: A New Diagnostic Procedure for Nipple Discharge," Jpn. J. Clin. Oncol., 1991, 21(3): 188–193.*

A. Okazaki et al., "Relationship Between Cytologic Results and the Extent of Intraductal Spread in Nonpalpable Breast Cancers with Nipple Discharge," Tumor Res., 1996, 31: 89–97.*

A. Okazaki et al., Nippon Geka Gakkai Zasshi, 97 (5): 357–362.

Osborne, J. Australas Radiol., 1989, 33(3): 266–269.

N. Petrakis, "Physiologic, Biochemical, and Cytologic Aspects of Nipple Aspirate Fluid," Breast Cancer Research and Treatment, 1986, 8: 7–19.

N. Petrakis et al., "Letters to the Editor: 'Prognostic Significance of Atypical Epithelial Hyperplasia in Nipple Aspirates of Breast Fluid,'" The Lancet, Aug. 1987, pp. 505.

N. Petrakis, "Studies on the Epidermiology and Natural History of Benign Breast Disease and Breast Cancer Using Nipple Aspirate Fluid," Cancer Epidemiology, Biomarkers & Prevention, 1993, 2: 3–10.

N. Petrakis, "Nipple Aspirate Fluid in Epidemiologic Studies of Breast Disease," Epidemiologic Reviews, 1993, 15: 188–195.

Pinkus et al., Am. J. Clin. Pathol., 1986, 85: 269–277, abstract.

O. Sartorius, "Fluid Cytology and Contrast Ductography," pp. 79–89.

O. Sartorius et al., "Contrast Ductography for Recognition and Localization of Benign and Malignant Breast Lesions: An Improved Technique," W. Logan, ed., Breast Carcinoma, New York, Wiley, 1977, pp. 281–300.

O. Sartorius, "The Biochemistry of Breast Cyst Fluids and Duct Secretions," Breast Cancer Research and Treatment, 1995, 35: 255–266.

Sawaf et al., Pathol. Biol. (Paris), 1992, 40: 655–665, Abstract.

Stanec et al., Lijec Vjesn., 1993, 115: 17–20, abstract.

Sundstrom et al., Int. J. Biol. Markers, 1994, 9: 102–108, abstract.

Tabar et al., Radiology, 149(1): 31–38.

Taylor–Papadimitriou et al., J. Cell Sci., 1989, 94: 403–413.

Van Zee et al., Cancer, 1998, 82: 1874–1880.

F. Weaver et al., "Management of Postoperative Lyphatic Leaks by Use of Isosulphan Blue [3]," Jnl. of Vascular Surgery, 1991, 14(4): 566–567.

M. Wrensch et al., "Breast Fluid Cholesterol and Cholesterol β–Epoxide Concentrations in Women with Benign Breast Diseasem," Cancer Research, 1989, 49: 2168–2174.

M. Wrensch et al., "Factors Associated with Obtaining Nipple Aspirate Fluid: Analysis of 1428 Women and Literature Review," Breast Cancer Research and Treatment, 1990, 15: 39–51.

M. Wrensch et al., "Breast Cancer Incidence in Women with Abnormal Cytology in Nipple Aspirates of Breast Fluid," Am. J. Epidemiol., 1992, 135(2): 130–141.

M. Wrensch et al., "Breast Cancer Risk Associated with Abnormal Cytology in Nipple Aspirates of Breast Fluid and Prior History of Breast Biopsy," Am. J. Epidemiol., 1993, 137(8): 829–833.

Zimmer et al., Virchows Arch. B Cell Pathol. Incl. Mol. Pathol., 1985, 49: 161–173, abstract.

* cited by examiner

METHODS FOR PERFORMING MEDICAL PROCEDURES WITHIN A BREAST DUCT

RELATED APPLICATIONS

This application is a continuation-in-part application and claims priority under 37 CFR 120 to U.S. application Ser. No. 09/153,564 filed Sep. 15, 1998 now U.S. Pat. No. 6,455,027, which is a continuation-in-part application of U.S. application Ser. No. 08/931,786, filed Sep. 16, 1997, now U.S. Pat. No. 6,168,779; and this application is a continuation-in-part and claims priority under 37 CFR 120 to U.S. application Ser. No. 09/740,561 filed Dec. 19, 2000 now abandoned which is a continuation application of U.S. application Ser. No. 09/067,661, filed Apr. 28, 1998, now U.S. Pat. No. 6,221,622, the contents of each of which are incorporated herein by reference.

The invention disclosed in this application was made with government support under U.S. Army Medical Research Grant Nos. DAMD17-94-J-4281 and DAMD17-96-C-6117. The government may have certain rights in the invention.

BACKGROUND OF THE INVENTION

1. Field of the Invention

The present invention relates generally to medical methods and devices for accessing body lumens and in particular to methods and apparatus for identifying ductal orifices in human breasts and accessing the ducts through the identified orifices.

Breast cancer is the most common cancer in women, with well over 100,000 new cases being diagnosed each year. Even greater numbers of women, however, have symptoms associated with breast diseases, both benign and malignant, and must undergo further diagnosis and evaluation in order to determine whether breast cancer exists. To that end, a variety of diagnostic techniques have been developed, the most common of which are surgical techniques including core biopsy and excisional biopsy. Recently, fine needle aspiration (FNA) cytology has been developed which is less invasive than the surgical techniques, but which is not always a substitute for surgical biopsy.

A variety of other diagnostic techniques have been proposed for research purposes. Of particular interest to the present invention, fluids from the breast ducts have been externally collected, analyzed, and correlated to some extent with the risk of breast cancer. Such fluid collection, however, is generally taken from the surface of the nipple and represents the entire ductal structure. Information on the condition of an individual duct is generally not provided. Information on individual ducts can be obtained through cannulation and endoscopic examination, but such examinations have been primarily in women with nipple discharge or for research purposes and have generally not examined each individual duct in the breast.

Since breast cancer usually arises from a single ductal system and exists in a precancerous state for a number of years, endoscopy in and fluid collection from individual breast ducts holds great diagnostic promise for the identification of intermediate markers. Much of the promise, however, cannot be realized until access to each and every duct in a patient's breast can be assured. Presently, ductal access may be obtained by a magnification of the nipple and identification of ductal orifice(s) using conventional medical magnifiers, such as magnification loupes. While such magnified examination is relatively simple, it cannot be relied on to identify all orifices. Moreover, the ductal orifices can be confused with other tissue structures, such as sebaceous glands and simple keratin-filled caruncles of the nipple. Thus, before ductal techniques can be further developed for diagnostic, research, or other purposes, it will be useful to provide methods and apparatus which facilitate identification of ductal orifices to distinguish them from other orifices, and allow subsequent ductal access in selected and/or all ducts in each breast.

2. Description of the Background At

Publications by the inventors herein relating to breast duct access include Love and Barsky (1996) Lancet 348: 997–999; Love (1992) "Breast duct endoscopy: a pilot study of a potential technique for evaluating intraductal disease," presented at 15th Annual San Antonio Breast Cancer Symposium, San Antonio, Tex., Abstract 197; Barsky and Love (1996) "Pathological analysis of breast duct endoscoped mastectomies," Laboratory Investigation, Modem Pathology, Abstract 67. A description of the inventors' breast duct access work was presented in Lewis (1997) Biophotonics International, pages 27–28, May/June 1997.

Nipple aspiration and/or the introduction of contrast medium into breast ducts prior to imaging are described in Sartorius (1995) Breast Cancer Res. Treat. 35: 255–266; Sartorius et al. (1977) "Contrast ductography for the recognition and localization of benign and malignant breast lesions: An improved technique," in: Logan (ed.), Breast Carcinoma, New York, Wiley, pp. 281–300; Petrakis (1993) Cancer Epidem. Biomarker Prev. 2: 3–10; Petrakis (1993) Epidem. Rev. 15: 188–195; Petralkis (1986) Breast Cancer Res. Treat 8: 7–19; Wrensch et aL (1992) Am. J. Epidem. 135: 130–141; Wrensch et al. (1990) Breast Cancer Res. Treat. 15: 39–51; and Wrensch et al. (1989) Cancer Res. 49: 2168–2174. The presence of abnormal biomarkers in fine needle breast aspirates is described in Fabian et al. (1993) Proc. Ann. Meet. Am. Assoc. Cancer Res. 34: A1556. The use of a rigid 1.2 mm ductoscope to identify intraductal papillomas in women with nipple discharge is described in Makita et aL (1991) Breast Cancer Res. Treat. 18: 179–188. The use of a 0.4 mm flexible scope to investigate nipple discharge is described in Okazaki et aL (1991) Jpn. J. Clin. Oncol. 21: 188–193. The detection of CEA in fluids obtained by a nipple blot is described in inayama et aL (1996) Cancer 78: 1229–1234. Delivery of epithelium-destroying agents to breasts by ductal cannulation is described in WO 97/05898.

SUMMARY OF THE INVENTION

The present invention provides improved methods, kits, and other apparatus for locating breast ducts in the breasts of human female patients. In particular, the methods of the present invention permit reliable identification of the orifices within the nipple of a breast which lead to each of the multiple ductal networks within the breast. By reliably identifying each office, all of the ductal networks can be located and subsequently accessed for diagnostic, risk assessment, therapeutic, research, or other purposes.

In a first aspect of the present invention, a method for locating an orifice of a breast duct comprises labelling ductal cells disposed at the ductal orifice with a visible or otherwise detectable label. The orifice may then be located based on the presence of the label at the orifice. Specific and preferred methods for labeling the orifices are described below in connection with a second aspect of the present invention. After the orifices have been located, an access device, such as a catheter or fiberoptic viewing scope, can be introduced through at least one of the orifices and into the associated breast duct. The method may further comprise introducing the same or a different access device through other orifices, often into each of the orifices to permit diagnosis, treatment, or other evaluation of all of the ductal networks of a breast.

In a second aspect, the present invention comprises a method for labelling the orifice of a breast duct. The method includes treating a nipple to expose tissue in an orifice of each duct. The treated nipple is then exposed to a labelling reagent capable of specifically binding to a tissue marker characteristic of tissue at the ductal orifice. Binding of the labelling reagent to the tissue results in immobilization of a label at the orifice, permitting subsequent location of the orifice as described above. The treating step preferably comprises washing the nipple with a kcratinolytic agent, such as 5% to 50% acetic acid (by weight), to remove keratin-containing materials which normally occlude the duct orifice and which could inhibit binding of the labelling reagent to the tissue marker. The tissue marker is typically characteristic of the ductal epithelium and represents either a membrane antigen or a cytoplasmic antigen. It has been found by the inventors herein that the ductal epithehum extends to within 0.1 mm to 0.2 mm of the nipple orifice and is sufficiently exposed to the surface of the nipple to permit labelling according to the methods of the present invention. Exemplary markets include cytokeratins, such as cytokeratin 8, cytokeratin 18, E cadherin, epithelial membrane antigen (EMA), and the like. Usually, the labelling reagent comprises a polycloral or monoclonal antibody or other specific binding substance specific for the marker. The antibody may be directly labelled with a visible label, such as a fluorescent label, a dye label a chemiluminescent label, or the like. Alternatively, the labeling reagent may comprise two or more components, typically including a primary antibody which is specific for the marker and one or more secondary binding substances which bind to the primary antibody and provide a label optionally a magnified label. For example, the primary antibody may be unlabeled, and a secondary labelled antibody specific for the primary antibody also be provided. As a further alternative, the primary antibody can be labelled with biotin or other hapten, and binding of the label provided via avidin, secondary antibody specific for the hapten, or the like. Numerous specific techniques for labelling of antigenic tissue markers are well known and reported in the immnocytochemical staining literature.

In a third aspect, a method according to the present invention comprises labelling cellular material at a ductal orifice with a visible label and subsequently accessing the duct through the labelled orifice. The labeling step usually comprises the method set forth above. The accessing step may comprise introducing an access device through at least one of the labelled orifices, and preferably through all of the labelled orifices, where the access device may be a catheter, a fiber optic viewing scope, or the like.

In a fourth aspect of the present invention, a kit for labelling breast duct orifices comprises a labelling reagent or reagents capable of specifically labelling a cellular marker at the ductal orifice, instructions setting forth a labelling method as described above, and a package containing the labelling reagent and the instructions for use. Usually, the kits of the present invention will further include the ketatinolytc agent and any other reagents that may be necessary for performing the method. Instructions for use will set forth the use of all provided reagents and may further set forth the use of agents which are available in the laboratory where the assay is to be performed.

In a fifth aspect of the present invention, a kit for accessing a breast duct comprises a labelling reagent capable of specifically labelling a ductal orifice and optionally a keratinolyric agent for treating the nipple prior to exposure of the labelling reagent. The kit further comprises an access device capable of being inserted through a labelled ductal orifice to a ductal lumen, such as a catheter, a fiber optic viewing scope, or the like. The kit still further comprises a package containing the labelling reagent, optionally the keratinolytic agent, and the access device. The accessing kit may further comprise instructions for use setting forth a method comprising the accessing steps as described above.

DESCRIPTION OF THE SPECIFIC EMBODIMENTS

Figure 1:
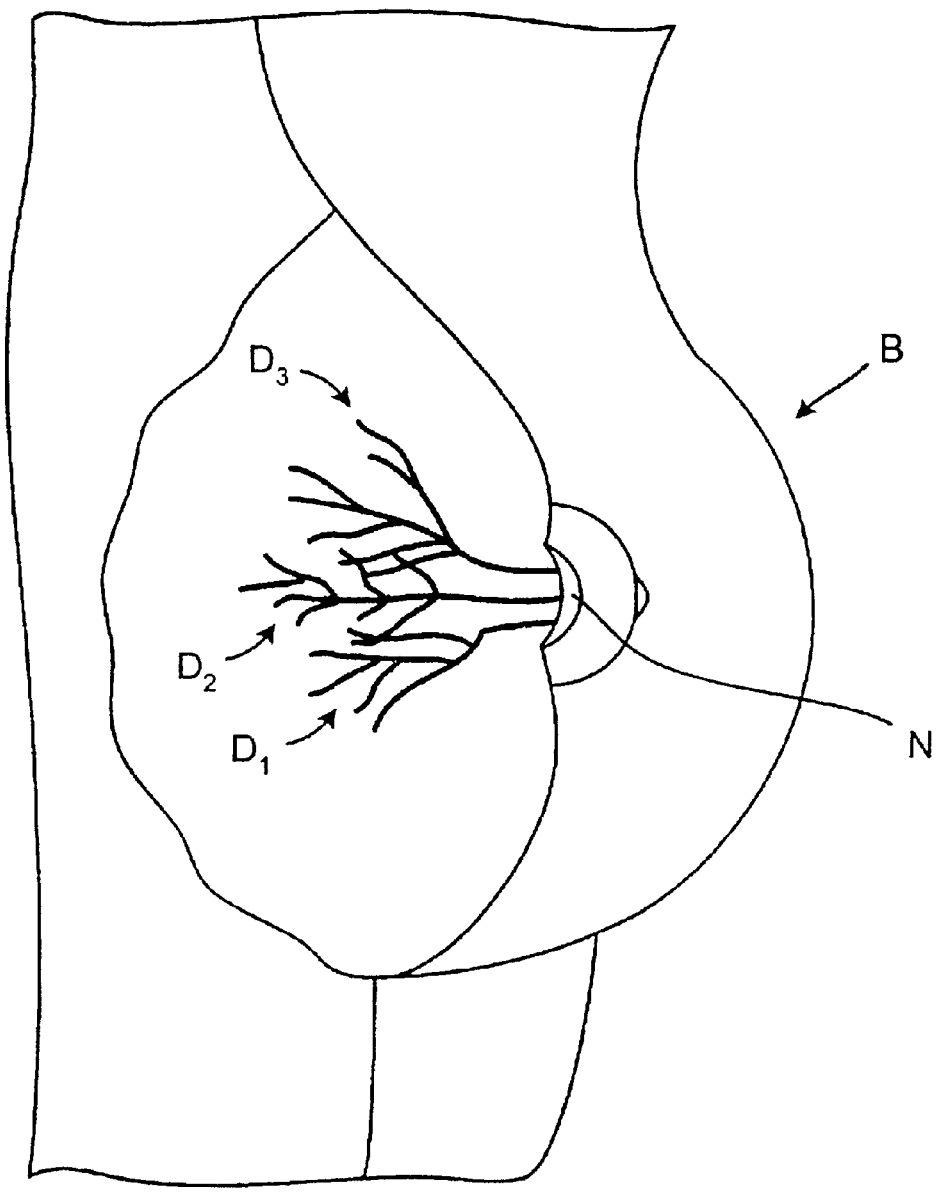
FIG. 1 is an anterior view of a human female breast, shown in section, and illustrating three of the six to nine ductal networks extending inwardly from the nipple.

The present invention comprises methods for locating, labeling, and accessing the ductal networks in human female breasts. A typical breast B is illustrated in FIG. 1 and includes a nipple N and from six to nine ducts D.

Figure 2:
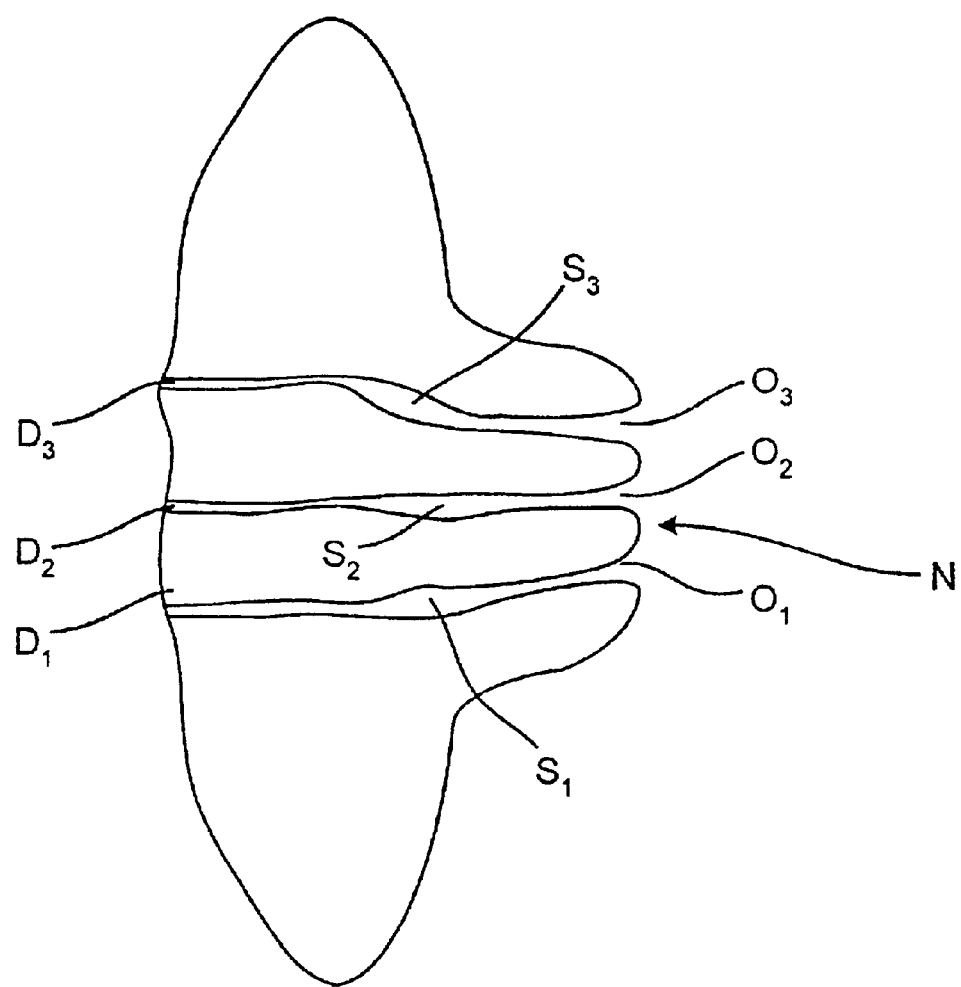
FIG. 2 is an enlarged view of the nipple of FIG. 1 illustrating the orifices leading to each of the three ductal networks.

Three ductal networks $D_{1-3}$ extending inwardly from the nipple N into the breast tissue are illustrated As best seen in FIG. 2, each ductal network $D_{1-3}$ begins with an orifice $O_{1-3}$ which lies at the surface of the nipple N and extends inwardly through a ductal sinus $S_{1-3}$ and then into a branching network. Each network D comprises a series of successively smaller lumens which are arranged in complex, three-dimensional patterns. The networks of each duct will overlap within the breast tissue but will not be interconnected. The present invention relies on identifying and labelling tissue in the orifice O of each duct D within the nipple N. Usually, there will be from six to nine orifices which open into a like number of ductal networks. An abrupt transition from the ductal epithelium to the squamous epithelium of the skin is found within about 0.1 mm to 0.2 mm of the nipple surface. Typically, the ductal orifice will be occluded with a conical keratin plug measuring about 0.5 mm to 1 mm in size.

The present invention relies on the specific labelling of tissue markers at the orifice of selected one(s) or all of the ductal network(s). By "specific," it is meant that the label will be introduced in a manner such that it will bind to the orifice region within the nipple but not bind (or will bind to a significantly lesser extent, usually at least 10-fold less) to other regions of the nipple. In this way, binding of the label to the orifice will be a discernable indication that the orifice is present and available for access to the associated ductal network.

In a particular aspect of the present invention, the tissue marker(s) will be an antigenic or epitopic site characteristic of the epithelial lining of the breast duct. Surprisingly, it has been found that the epithelial lining extends sufficiently far into the orifice region of the duct to permit successful labelling using generally conventional immunocytochemical labelling reagents and techniques, as described in more detail below. Exemplary tissue markers include antigens and epitopes defined by the cytokeratins present in the epithelial cytoplasmic lining, such as cytokeratin 8, cytokeratin 18, and by molecules present in the membrane lining, such as E cadherin, epithelial membrane antigen (EMA), and the like. Suitable breast epithelial tissue markers are described, for example, in Moll et al. (1982) Cell 30:11–19; Gown and Vogel (1984) Am. J. Pathol. 114:309–321; and Johnson (1991) Cancer Metastasis Rev. 10:11–22.

Figure 3:
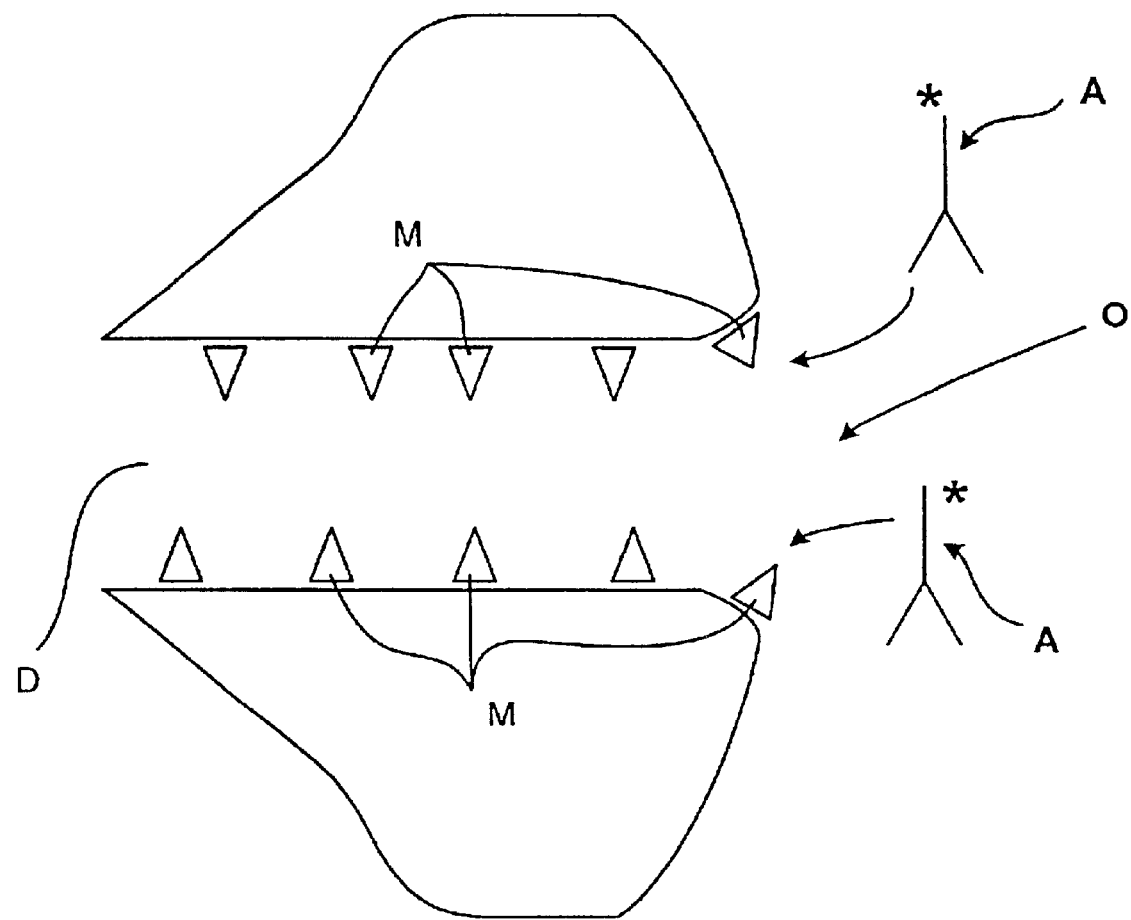
FIG. 3 is a still further enlarged view of a single orifice illustrating the distribution of tissue markets from the epithelium to the opening of the orifice, where such markers at the opening are available for binding to labelled antibodies.
Figure 4:
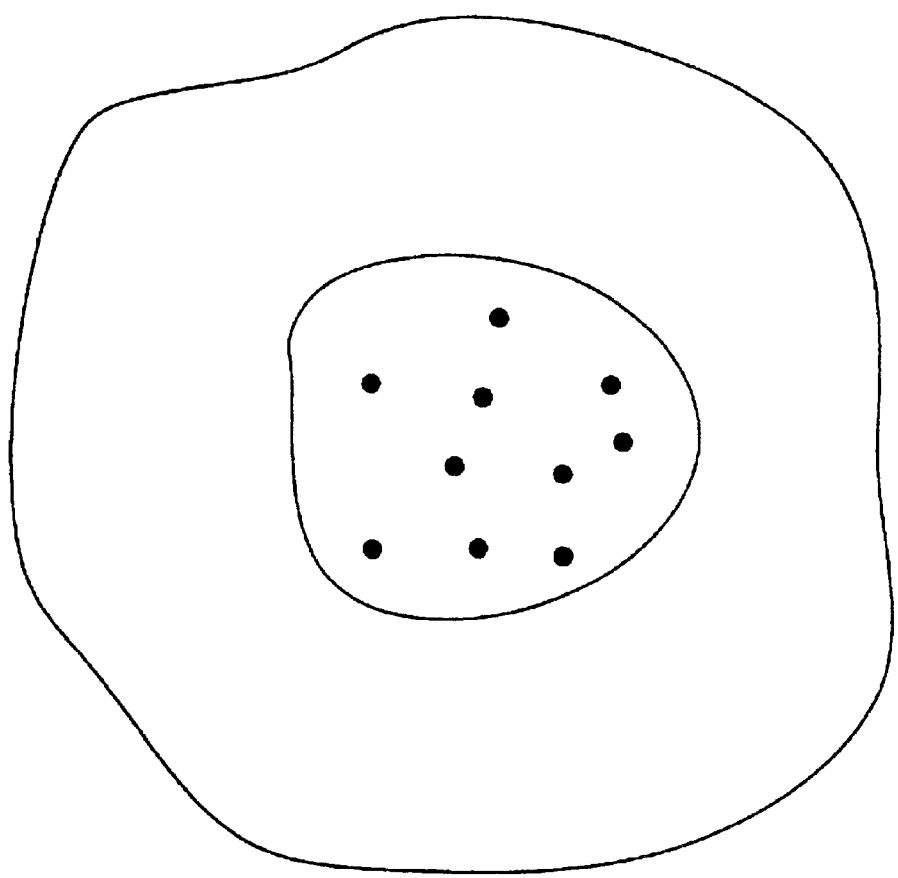
FIG. 4 is a schematic illustration of the appearance of a nipple which has been labelled with visible markers according to the methods of the present invention.

Referring now to FIG. 3, an orifice region O of a ductal network D is illustrated with a plurality of markers M lining the epithelium of the duct and extending to the perimeter of the orifice. Labelled antibodies A can be used to locate and label those markers M which are near the orifice O. Frequently, it ill be desirable or necessary to wash the nipple with a solution capable of unblocking the orifice to permit binding of the antibodies or other labelling reagent. For example, the orifice can frequently become plugged with keratin-contain materials, and washing with a keratinolytic solution, such as acetic acid (5% to 50% by weight) admixed in a pharmaceutical delivery vehicle, will expose sufficient marker sites at each orifice to enable labelling according to the methods of the present invention.

The labelled antibodies or other labelling reagents may be formulated as liquid, typically aqueous, solutions in a generally conventional manner. Suitable anti-cytokeratin antibodies may be obtained from commercial suppliers, with specific antibodies including FITC-anticytokeratin (Becton-Dickenson), CAM 5.2, and the like. The antibodies may be coupled to one member of a signal-producing system capable of generating a detectable visual or other change on the tissue surface, where an element will be referred to here and after as a "visual label" Suitable signal-producing systems include fluorescent systems, color-generating systems, and luminescent systems. Preferred is use of fluorescent systems which comprise a single fluorescent label, but other systems which comprise two or more components including enzymes, substrates, catalysts, enhancers, and the like, may also be employed. At least one component of the signal-producing system will be attached to the antibody or other specific binding substance which is capable of directly or indirectly binding to the tissue marker. Usually, the antibody will bind directly to the tissue marker, but it will also be possible to employ primary antibodies which are specific for the tissue marker and labelled secondary antibodies which introduce the label or component of the signal-producing system. For example, the primary antibody can be mouse IgG and the labelled secondary antibody can be FITC goat anti-mouse IgG (Zymcd). Such signal-producing systems and the use on tissue and tissue samples is well described in the medical, scientific, and patent literature relating to immunocytochemical staining.

In an exemplary protocol according to the present invention, the nipple is first dekeratinized with 5% to 50% acetic acid to remove keratin and other potentially blocking and contaminating substances from the ductal orifices. A solution of the labelled antibody, preferably an antibody which directly binds to a cytokeratin or other epithelial cytoplasmic or surface membrane marker, such as the antibodies described above, is then applied to the nipple surface. The antibody is preferably linked to a fluorescent marker, more preferably fluorescein, and the fluorescein-labelled antibody delivered in a buffered aqueous solution. Optionally, controls may be run. For example, labelled antibodies of the same Ig class as the specific antibody may be exposed to the nipple at the same dilution. By comparing the results with the specific antibody and the control antibody, non-specific binding can be discounted.

The labelling reagent will typically be packaged (optionally with the keratinolytic agent) together with instructions for use in a conventional assay package, such as a box, bottle, tube, pouch, or the like. The instructions for use may be written out on a separate instruction sheet or may be partially or fully incorporated onto the packaging materials.

A second kit according to the present invention will comprise the labelling reagent (optionally with the keratinolytic agent) in a package as set forth above. The package will further include an access device capable of being introduced through the ductal orifice, such as a catheter, a fiber optic scope, or the like. Suitable catheters and fiber optic scopes are described in the background art discussed above. Such kits may further comprise instructions for use (IFU) setting forth any of the methods described above.

The following experimental descriptions are offered by way of illustration, not by way of imitation.

EXPERIMENTAL

A. Dekeratinizing the Nipple

Acetic acid is mixed with Velvacrol (50% v/w), a pharmaceutical vehicle comprising an aqueous mixture of petrolatum/mineral oil, acetyl alcohol, sodium laural sulfate, cholesterol, methylparaben, butylparaben, and propylparaben. To keep the acetic acid in solution, mcthyl cellulose (100 mg) is pre-added to the Velvacrol (5 g). The mixture possesses a uniform pasty consistency and is applied to the nipple as an ointment or paste. The keratinolhtic agent is typically left on the nipple for twenty-four hours or longer to remove the keratin plugs from the ductal orifices.

B. Labelling of the Ductal Orifice

For cytoplasmic antigens, the ductal epithelium must be solubilized with 70% by weight ethanol. For a membrane or surface antigen, the solubilization step is not necessary. A mouse monoclonal primary antibody is used as a dilution of 1:5 to 1:100 and maintained on the nipple for one hour at room temperature. After such incubation, the nipple is washed with phosphate buffered saline PBS and a secondary antibody (fluoresceinated goat anti-mouse antibody) used at a dilution of from 1:5 to 1:1000 fold at room temperature. After washing with PBS, the nipple may be examined under ultraviolet (UV) light at a wavelength selected for the particular fluoroclrome being used. A control can then be run using an antibody of a similar class, but without specificity for any of the ductal epithelial or other markers which may be present on the nipple. This method will provide successful labelling of the ductal orifices and permit subsequent cannulation and examination of each orifice.

C. Ductoscopy

Duct cannulation and exploration can be performed under white (visual) light. One or more ducts are cannulated first with a rigid metal duct-probe (6 Fr Taber-Rothschild Galactography Kit, Manan Medical Products Inc., Northbrook, Ill.) dilated to 0.45 mm to 0.5 mm. A guide wire (0.4 mm) is then inserted, and a catheter passed over the guide wire. Physiological saline (0.2 ml to 0.5 ml) is instilled to wash the duct lumen. The washings may be spun down and analyzed cytologically.

The duct lumen is then dried by injecting 0.2 ml to 0.5 ml air. At the end of the final insufflation, the orifice is held shut by pinching the end of the nipple. An endoscope (FVS-3000, M&M Company, Tokyo), which is 0.4 mm in outer diameter is then threaded into the duct orifice while dilation of the duct with air is maintained. After the endoscope is inserted for 5 mm to 10 mm, its position may be confirmed. The cannulization may then be continued as far distauly as possible. Desired diagnostic, therapeutic, or other material may then be instilled into the duct Alternatively, after cannulation, the duct may be dilated with saline using a closed system with a burst adapter to allow a better view.

In a particular aspect of the present invention, cells may be removed through the cannula (as washings). The collected cells may be processed according to standard cytological methods for similar washings, such as bronchial washings and biopsy specimens. The cells may be identified directly or indirectly by histopathological analysis of the duct from which the cells were obtained.

Although the foregoing invention has been described in detail for purposes of clarity of understanding, it will be obvious that certain modifications may be practiced within the scope of the appended claims.

What is claimed is:

1. A method for performing a medical procedure within a breast duct, said method includes the steps of:
   introducing a guiding member into said breast duct;
   traducing and positioning a member having an internal lumen in said breast duct;
   introducing a wash fluid into said breast duct through said internal lumen;
   removing washings from said breast duct through said internal lumen; and
   collecting said washings for cytological analysis.

2. The method of claim 1 wherein the collected washings include cellular material from within said breast duct.

3. The method of claim 1 wherein said wash fluid includes saline.

4. The method of claim 1 wherein said member having an internal lumen includes a catheter; and wherein said step of introducing and positioning said member having said internal lumen includes a step of passing said catheter over said guiding member.

5. The method of claim 4 wherein said catheter is passed over said guiding member after said guiding member is positioned within said breast duet.

6. The method of claim 1 wherein said guiding member includes a guidewire; and the method further includes the step of dilating said breast duct before said guidewire is inserted in said breast duct.

7. The method of claim 6 wherein said dilating step includes the step of cannulating said breast duct.

8. The method of claim 7 wherein said cannulating step includes introducing a rigid duct-probe into said breast duct.

9. The method of claim 1 wherein said medical procedure includes the step of performing a ductoscopy.

10. The method of claim 9 wherein said ductoscopy includes the step of positioning an endoscope within said duct for viewing the interior of said duct from which said washings are removed.

11. A method for obtaining cellular material from within a breast duct during a medical procedure, said method includes the steps of:
    introducing a member having an internal lumen within said breast duct;
    introducing a fluid into said breast duct;
    introducing an endoscope within said breast duct;
    viewing the interior of said breast duct using said endoscope;
    removing cellular washings from said breast duct, wherein said step of removing said cellular washings includes removing said cellular washings through said internal lumen.

12. The method of claim 11 wherein said method further includes the step of positioning a catheter within said breast duct, and wherein said fluid is introduced into said breast duct through said catheter.

13. The method of claim 12 wherein said cellular washings are removed from within said duct through said catheter.

14. The method of claim 11 wherein said member having said internal lumen includes a device that cannulates an opening to said breast duct.

15. The method of claim 14 wherein said device includes a ductal probe.

16. The method of claim 11 wherein said medical procedure includes a ductoscopy.

17. A method for obtaining cellular material from within a breast duct during a medical procedure, said method includes the steps of:
    introducing and positioning a catheter in said breast duct;
    introducing a wash fluid into said breast duct through said catheter;
    removing washings from said breast duct through said catheter;
    collecting said washings for cytological analysis.

18. The method of claim 17 further including the step of introducing an optical scope into said breast duct for viewing the breast duct.

19. The method of claim 18 wherein said medical procedure includes a ductoscopy.

* * * * *

UNITED STATES PATENT AND TRADEMARK OFFICE
CERTIFICATE OF CORRECTION

PATENT NO. : 6,890,311 B2  
DATED : May 10, 2005  
INVENTOR(S) : Susan M. Love et al.

Page 1 of 1

It is certified that error appears in the above-identified patent and that said Letters Patent is hereby corrected as shown below:

Title page,
Item [56], References Cited, OTHER PUBLICATIONS,
"Grillo et al" reference, "Cynaecol" should read -- Gynaecol --.

Column 7,
Line 27, "traducing" should read -- introducing --.
Line 48, "in" should read -- into --.

Signed and Sealed this

Eleventh Day of October, 2005

JON W. DUDAS
*Director of the United States Patent and Trademark Office*